United States Patent
Basiri et al.

(10) Patent No.: US 12,322,490 B2
(45) Date of Patent: Jun. 3, 2025

(54) ARTIFICIAL INTELLIGENCE MODELS FOR VMAT SECTOR CALCULATIONS

(71) Applicant: Siemens Healthineers International AG, Steinhausen (CH)

(72) Inventors: Shahab Basiri, Siuntic (FI); Esa Kuusela, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 252 days.

(21) Appl. No.: 18/194,232

(22) Filed: Mar. 31, 2023

(65) Prior Publication Data

US 2024/0331836 A1  Oct. 3, 2024

(51) Int. Cl.
 *G16H 20/40* (2018.01)
(52) U.S. Cl.
 CPC .................. *G16H 20/40* (2018.01)
(58) Field of Classification Search
 None
 See application file for complete search history.

(56) References Cited

U.S. PATENT DOCUMENTS

| | | | | |
|---|---|---|---|---|
| 2020/0164225 A1* | 5/2020 | Zhang | .................. | A61N 5/1031 |
| 2021/0299469 A1* | 9/2021 | Harju | .................. | A61N 5/1064 |
| 2022/0088410 A1 | 3/2022 | Hibbard | | |
| 2022/0093242 A1* | 3/2022 | Hakala | .................. | G16H 70/20 |
| 2022/0184419 A1* | 6/2022 | Basiri | .................. | A61N 5/1038 |
| 2022/0296924 A1 | 9/2022 | Peltola et al. | | |
| 2022/0415472 A1* | 12/2022 | Hakala | .................. | G06N 3/092 |
| 2024/0207645 A1* | 6/2024 | Hibbard | .............. | A61N 5/1081 |

FOREIGN PATENT DOCUMENTS

| | | |
|---|---|---|
| CN | 114206438 A | 3/2022 |
| CN | 115361998 A | 11/2022 |

OTHER PUBLICATIONS

Ugurlu et al. The impact of the field width on VMAT plan quality and the assessment of half field method, Journal of Appl Clin Med Phys 2020; 21:3:115-122.*
International Search Report dated Jun. 18, 2024 for PCT App.PCT/EP2024/056505 (2 pages).

* cited by examiner

*Primary Examiner* — David J Stoltenberg
(74) *Attorney, Agent, or Firm* — Foley & Lardner LLP (57) ABSTRACT

Disclosed herein are systems and methods for iteratively training artificial intelligence models using reinforcement learning techniques including a method comprising executing, using at least one patient attribute, a number of arcs, and at least one clinical goal attribute associated with a volumetric modulated arc therapy (VMAT) treatment of a patient, an artificial intelligence model configured to predict a number of control points and a number of dose calculation sectors for the VMAT treatment, the artificial intelligence model having been iteratively trained using a reinforcement learning method, where with each iteration, the artificial intelligence model transmits one or more test control point and one or more test dose calculation sector to a plan optimizer model configured to predict a treatment plan, and trains a policy in accordance with calculated rewards.

20 Claims, 6 Drawing Sheets

ARTIFICIAL INTELLIGENCE MODELS FOR VMAT SECTOR CALCULATIONS

TECHNICAL FIELD

This application relates generally to generating, training, and operating artificial intelligence (AI) computer models to predict radiation therapy treatment plans.

BACKGROUND

Radiation therapy (radiation-based therapy or radiotherapy) is a cancer treatment wherein high doses of radiation that can kill cancerous cells or shrink a tumor are applied the affected area. The target region of a patient's body that is intended to receive radiation (e.g., tumor) is referred to as the planning target volume (PTV). The goal is to deliver enough radiation to the PTV to kill the cancerous cells (also referred to herein as a treatment plan or radiation therapy treatment). However, other organs or anatomical regions that are adjacent to or surround the PTV can be in the path of radiation beams and can receive enough radiation to be damaged or harmed. These organs or anatomical regions are referred to as organs at risk (OARs). Usually, a physician or a radiologist identifies both the PTV and the OARs before radiation therapy by using, for example, computed tomography (CT) images, magnetic resonance imaging (MRI) images, positron emission tomography (PET) images, images obtained via other imaging modalities, or a combination thereof.

Using the medical images of the patient, as well as the identified PTV and the OARs, a team of medical professionals (e.g., physicians, radiologists, oncologists, radiology technicians, other medical personnel, or a combination thereof) determines the radiation parameters to be used during the radiation therapy treatment. These radiation parameters may include, for example, the type, angle, intensity, and/or the shape of each radiation beam. In determining these parameters, the team attempts to achieve a radiation dose distribution to the patient that meets predefined criteria (also referred to herein as the plan objectives or clinical objectives).

To optimize the radiation parameters in a way that meets the predefined criteria, a software solution(s) or a computer model(s)(typically referred to as "plan optimizers") are utilized that can run a plurality of simulations having various radiation parameters and can select, based on the simulation results, a final set of radiation parameters to be used. These radiation parameters are typically referred to as a radiation therapy treatment plan (RTTP). However, this process can be highly inefficient because plan optimizers typically use an iterative, trial-and-error process to determine various attributes of the RTTP. For instance, after the treating physician inputs the objectives, the software solution iteratively analyzes different possibilities (e.g., different iterations of varying attributes within a large search space) to identify one or more beam geometry attributes that yield the best or acceptable results. As a result, the software solutions may require substantial computing resources and may not produce timely results.

For instance, the radiation parameters may include volumetric modulated arc therapy (VMAT) techniques, such as control points (CP). VMAT arc optimization is a non-convex problem defined in the very large search space of CP parameters. Solving this problem requires an efficient space exploration scheme. The commonly used computer models search for the optimal CP parameters within the large search space until the model converges upon a result. This process is undesirable because it requires high computing processing power and may not produce timely results.

SUMMARY

For the aforementioned reasons, there is a desire for a computer model to generate treatment attributes (specifically, VMAT arc attributes or CP attributes) using methods and systems that are not dependent on the technician's subjective interpretation or conventional computer modeling techniques. There is a further desire for an improved AI modeling/training technique that does not require extensive training datasets and is computationally efficient, cost-effective, and produces timely results.

In some embodiments, certain computer models (configured for VMAT arc optimization) conduct searches for the optimal CP parameters based on a progressive multi-resolution (MR) method. In this method, at the beginning of every MR level, (1) the arc fields are partitioned into multiple dose calculation sectors (DCS); (2) iterative subsets of DCS candidates are selected for calculating dose gradient updates; and (3) the MR levels with which to proceed are determined, based on the convergence status of the optimizer.

The above sector commissioning tasks have a positive impact on the final plan quality, as well as the convergence speed of the plan optimizer. For instance, the method of partitioning the arc fields may affect the speed of finding beneficial dose delivery angles. In addition, the determined solution to the optimization problem could be heavily biased toward the DCS candidates selected at earlier stages of the optimization process. Finding optimal policies in performing sector commissioning tasks requires solving complex sub-problems. This may slow down the optimization of the treatment plans. Often, computer models used for VMAT arc optimization utilize policies that do not yield suitable results, such as selecting (sometimes at random) a fixed number of DCSs), which may provide reasonable solutions for some treatment cases, but may lead to suboptimal solutions at slow convergence rates for others.

The methods and systems discussed herein solve this technical problem by utilizing a modern machine learning method, where a trained AI policy is used to optimally commission the sectors for each specific treatment case. In addition, the agent (the AI model's policy) performs the commissioned tasks at a much faster rate than the conventional methods.

Using the methods and systems discussed herein, a computer (or processor or server) can train (e.g., using reinforcement learning methods) and execute an AI model, such that the AI model can predict the optimal way of partitioning the field arc into a number of sectors, where each sector has a certain number of CPs (depending on the complexity of the fluence map in that sector). Certain conventional methods, such as manual methods, identify the sectors without accounting for patient-specific data, such as anatomical geometry. In contrast, the AI models discussed herein, partition the arc (at least partially) in accordance with patient-specific data. In this manner, (e.g., customizing the partitioning based on patient-specific data), better partitioning of the arc is attained, via which a plan optimizer may achieve convergence upon an RTTP using less computing power and/or in less time. Moreover, the number of CPs may be optimized using the methods and systems discussed herein. For instance, in some embodiments, the AI model may generate fewer CPs, which may lead to a plan optimizer achieving better results in less time.

In an embodiment, a method comprising executing, by a processor, using at least one patient attribute, a number of arcs, and at least one clinical goal attribute associated with a volumetric modulated arc therapy (VMAT) treatment of a patient, an artificial intelligence model configured to predict a number of control points and a number of dose calculation sectors for the VMAT treatment, the artificial intelligence model having been iteratively trained using a reinforcement learning method, where with each iteration, the artificial intelligence model: transmits one or more test control points and one or more test dose calculation sectors to a plan optimizer model configured to predict a treatment plan; and identifies a reward for the one or more test control point and the one or more test dose calculation sectors based on a performance value of the plan optimizer model using the one or more test control points and the one or more test dose calculation sectors, wherein the processor iteratively trains a policy of the artificial intelligence model based on maximizing the reward.

The method may further comprise transmitting, by the processor, the number of control points and the number of dose calculation sectors for the VMAT treatment to the plan optimizer model.

The reward may be based on whether the plan optimizer model converges upon a predicted treatment plan.

The reward may be based on an execution time of the plan optimizer model.

The artificial intelligence model may be configured to predict a degree associated with at least one control point.

The method may further comprise displaying, by the processor, a visual representation of at least one dose calculation sector.

The method may further comprise displaying, by the processor, a visual representation of at least one control point.

In another embodiment, a system may comprise a server in communication with an artificial intelligence model, where the server is configured to: execute using at least one patient attribute, a number of arcs, and at least one clinical goal attribute associated with a volumetric modulated arc therapy (VMAT) treatment of a patient, the artificial intelligence model configured to predict a number of control points and a number of dose calculation sectors for the VMAT treatment, the artificial intelligence model having been iteratively trained using a reinforcement learning method, where with each iteration, the artificial intelligence model: transmits one or more test control points and one or more test dose calculation sectors to a plan optimizer model configured to predict a treatment plan; and identifies a reward for the one or more test control points and the one or more test dose calculation sectors based on a performance value of the plan optimizer model using the one or more test control points and the one or more test dose calculation sectors, wherein the processor iteratively trains a policy of the artificial intelligence model based on maximizing the reward.

The server may be further configured to transmit the number of control points and the number of dose calculation sectors for the VMAT treatment to the plan optimizer model.

The reward may be based on whether the plan optimizer model converges upon a predicted treatment plan.

The reward may be based on an execution time of the plan optimizer model.

The artificial intelligence model may be configured to predict a degree associated with at least one control point.

The server may be further configured to display a visual representation of at least one dose calculation sector.

The server may be further configured to display a visual representation of at least one control point.

In another embodiment, a system comprises one or more processors; and a non-transitory memory configured to store computer code instructions, the computer code instructions when executed cause the one or more processors to: execute using at least one patient attribute, a number of arcs, and at least one clinical goal attribute associated with a volumetric modulated arc therapy (VMAT) treatment of a patient, an artificial intelligence model configured to predict a number of control points and a number of dose calculation sectors for the VMAT treatment, the artificial intelligence model having been iteratively trained using a reinforcement learning method, where with each iteration, the artificial intelligence model transmits one or more test control points and one or more test dose calculation sectors to a plan optimizer model configured to predict a treatment plan; and identifies a reward for the one or more test control points and the one or more test dose calculation sectors based on a performance value of the plan optimizer model using the one or more test control points and the one or more test dose calculation sectors, wherein the processor iteratively trains a policy of the artificial intelligence model based on maximizing the reward.

The computer code instructions may further cause the one or more processors to transmit the number of control points and the number of dose calculation sectors for the VMAT treatment to the plan optimizer model.

The reward may be based on whether the plan optimizer model converges upon a predicted treatment plan.

The reward may be based on an execution time of the plan optimizer model.

The artificial intelligence model may be configured to predict a degree associated with at least one control point.

The computer code instructions further cause the one or more processors to display a visual representation of at least one dose calculation sector.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Reference will now be made to the illustrative embodiments depicted in the drawings, and specific language will be used herein to describe the same. It will nevertheless be understood that no limitation of the scope of the claims or this disclosure is thereby intended. Alterations and further modifications of the inventive features illustrated herein, and additional applications of the principles of the subject matter illustrated herein that would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Figure 1:
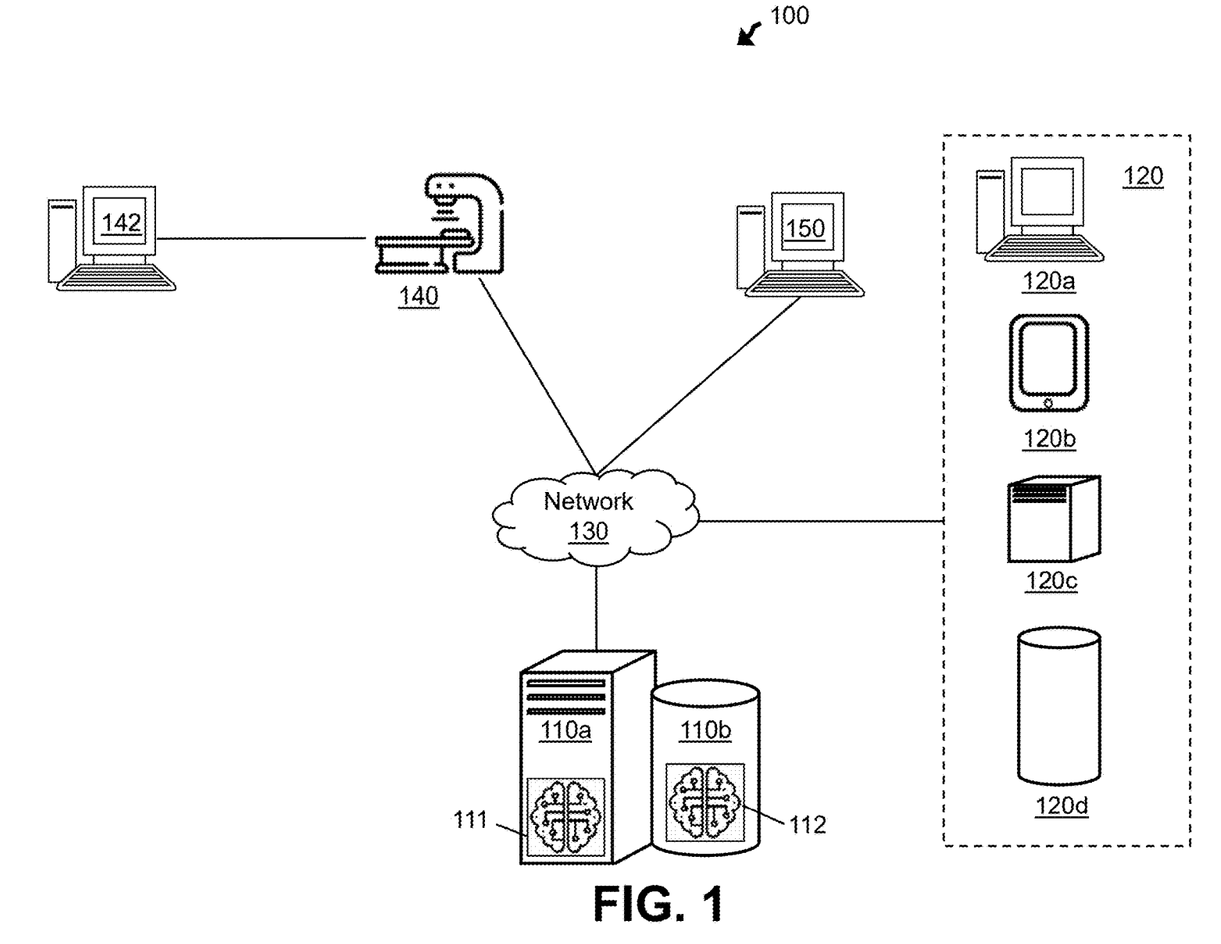
FIG. 1 illustrates components of an AI-enabled VMAT arc calculation system, according to an embodiment.

As will be described below, a central server (referred to herein as the analytics server) can retrieve data and train an AI model using various methods described herein to identify a suitable VMAT arc. FIG. 1 is a non-limiting example of components of a system in which the analytics server operates.

FIG. 1 illustrates components of an AI-enabled VMAT arc calculation system (system 100), according to an embodiment. The system 100 may include an analytics server 110a, system database 110b, VMAT arc calculation model 111, end-user devices 120a-d (collectively end-user devices 120), and an administrator computing device 150. Various components depicted in FIG. 1 may belong to a radiation therapy clinic at which patients may receive radiation therapy treatment via one or more radiation therapy machines (e.g., medical device 140) in the clinic. The above-mentioned components may be connected through a network 130. Examples of the network 130 may include, but are not limited to, private or public LAN, WLAN, MAN, WAN, and the Internet. The network 130 may employ wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, such as a GSM (Global System for Mobile Communications), CDMA (Code Division Multiple Access), or EDGE (Enhanced Data for Global Evolution) network.

The system 100 is not confined to the components described herein and may include additional or other components, not shown for brevity, which is to be considered within the scope of the embodiments described herein.

The analytics server 110a may generate and display an electronic platform configured to use various computer models 111-112 to identify attributes of an RTTP for a patient's treatment. The electronic platform may include a graphical user interface (GUI) displayed on the end-user devices 120 and/or the administrator computing device 150. An example of the electronic platform generated and hosted by the analytics server 110a may be a web-based application or a website configured to be displayed on different types of electronic devices, such as mobile devices, tablets, personal computers, and the like.

In a non-limiting example, a physician operating the physician device 120b may access the platform, input patient attributes, characteristics, and other data, and further instruct the analytics server 110a to generate an RTTP (including the beam angle). Additionally or alternatively, the analytics server 110a may optimize only one particular attribute of the RTTP (e.g., optimize beam angle only).

The analytics server 110a may recommend the RTTP (e.g., beam angles and other radiation parameters and/or treatment plan attributes) used for proton radiation, photon radiation, and electron radiation. In particular, analytics server 110a may utilize the methods and systems described herein to execute the VMAT arc calculation model 111 for identifying treatable sectors. Then, the analytics server 110a may use the generated treatable sectors to limit the search space used by the plan optimizer model 112. Further, the analytics server 110a may transmit the beam angles and other radiation parameters and/or treatment plan attributes to one or more other servers. Additionally or alternatively, the analytics server 110a (or another server) may adjust the configuration of one or more devices (e.g., the medical device 140) based on the optimized beam angle. For instance, the RTTP may be directly sent to the medical device 140 and/or the computer 142 that functionally controls the medical device 140.

The medical device 140 may be any medical device used in the radiation therapy treatment of a patient (such as a CT scan machine, radiation therapy machine (e.g., a linear accelerator, particle accelerator (including circular accelerators), or a cobalt machine)). The medical device 140 may also include an imaging device capable of emitting radiation such that the medical device 140 may obtain images according to various methods to accurately image the internal anatomical structure of a patient. For instance, the medical device 140 may include a rotating system (e.g., a static or rotating multi-view system). A non-limiting example of a multi-view system may include stereo systems (e.g., two systems arranged orthogonally).

The analytics server 110a may host a website accessible to users operating any of the electronic devices described herein (e.g., end-users or medical professionals), where the content presented via the various webpages may be controlled based upon each particular user's role or viewing permissions. The analytics server 110a may be any computing device comprising a processor and non-transitory, machine-readable storage capable of executing the various tasks and processes described herein. The analytics server 110a may employ various processors such as central processing units (CPU) and graphics processing units (GPU), among others. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each end-user devices 120. Different users may use the website to view and/or interact with the recommended (optimized) results. Different servers, such as a clinic server 120c may also use the recommended results in downstream processing.

The analytics server 110a may be configured to require user authentication based upon a set of user authorization credentials (e.g., username, password, biometrics, cryptographic certificate, and the like). The analytics server 110a may access the system database 110b configured to store user credentials, which the analytics server 110a may be configured to reference in order to determine whether a set of entered credentials (purportedly identifying the user) match an appropriate set of credentials that authenticate the user.

The analytics server 110a may generate and host webpages based upon a particular user's role within the system 100. In such implementations, the user's role may be defined by data fields and input fields in user records stored in the system database 110b. The analytics server 110a may authenticate the user and may identify the user's role by executing an access directory protocol (e.g., LDAP). The analytics server 110a may generate webpage content that is customized according to the user's role as defined by the user record in the system database 110b.

The analytics server 110a may receive various clinical objectives, patient data, and treatment data from the end-user devices 120. For instance, a physician may access the platform provided by the analytics server 110a using a physician device 120b. The physician may input various patient attributes and/or clinical objectives using one or more input elements of the platform. The analytics server 110a may then execute various methods discussed herein and display an RTTP on the platform.

The end-user devices 120 may be any computing device comprising a processor and a non-transitory machine-readable storage medium capable of performing the various tasks and processes described herein. Non-limiting examples of end-user devices 120 may be a workstation computer, laptop computer, tablet computer, and server computer. During operation, various users may use end-user devices 120 to access the GUI operated by the analytics server 110a. Specifically, the end-user devices 120 may include a clinic computer 120a, a physician device 120b, a clinic server 120c, or a clinic database 120d.

In order to generate the RTTP, the analytics server 110a may then execute various models (e.g., VMAT arc calculation model 111 and/or a plan optimizer model 112) to analyze the retrieved/received data.

The administrator computing device 150 may represent a computing device operated by a system administrator. The administrator computing device 150 may be configured to display beam angles, radiation parameters, and/or other radiation therapy treatment attributes generated by the analytics server 110a; monitor the VMAT arc calculation model 111 utilized by the analytics server 110a and/or end-user devices 120; review feedback; and/or facilitate training or retraining (calibration) of the models 111-112 that are maintained by the analytics server 110a.

The analytics server 110a may be in communication (real-time or near real-time) with the medical device 140 (or its computer 142), such that a server/computer hosting the medical device 140 can adjust the medical device 140 based on the RTTP (e.g., beam angles, treatment attributes and/or radiation parameters determined by the analytics server 110a). For instance, the radiation therapy machine may adjust the gantry, beam blocking device (e.g., multi-leaf collimator MLC), and couch based on optimized beam angles, where the optimized beam angle is an angle of the medical device 140 that emits radiation in a direction of the PTVs. The analytics server 110a may transmit instructions to the radiation therapy machines indicating any number or type of radiation parameters and/or treatment attributes to facilitate such adjustments.

The VMAT arc calculation model 111 and/or 112 may represent any collection of algorithmic logic and/or artificial intelligence models (e.g., using various machine learning techniques). For instance, the VMAT arc calculation model 111 may include various algorithms to identify attributes and characteristics of a treatable sector based on patient data and/or treatment attributes. Using the VMAT arc calculation model 111, the analytics server 110n may execute the plan optimizer model 112. For instance, the analytics server 110a may execute the models in conjunction with each other and then revise one or more configuration parameters of the plan optimizer 112. Non-limiting examples of a configuration parameter revised by the analytics server 110a may include a search space that is limited/revised using the attributes of the treatable sector. As a result, the efficiencies discussed herein can be achieved without revising the plan optimizer 112 itself. For instance, the VMAT arc calculation model 111 can be executed independently and used in conjunction with an existing plan optimizer. Therefore, the plan optimizer (or the system infrastructure) can be retrofitted using the methods and systems discussed herein. This minimal interference with existing infrastructure allows for the improvement of a plan optimizer without the need to revise its source code.

In some embodiments, the analytics server 110a may collect patient data from various sources not shown in FIG. 1. For instance, the analytics server 110a may monitor and collect patient and treatment attributes associated with previously-treated radiotherapy patients to include in a training dataset. Additionally or alternatively, the analytics server 110a may collect/aggregate other patient data (e.g., data associated with how a set of patients or clinical participants received their respective radiotherapy treatment). Using the collected data, the analytics server 110a may generate a training dataset with which the analytics server 110a can train the VMAT arc calculation model 111. As a result, the VMAT arc calculation model 111 may be used to limit the search space used by the plan optimizer 112.

Figure 2:
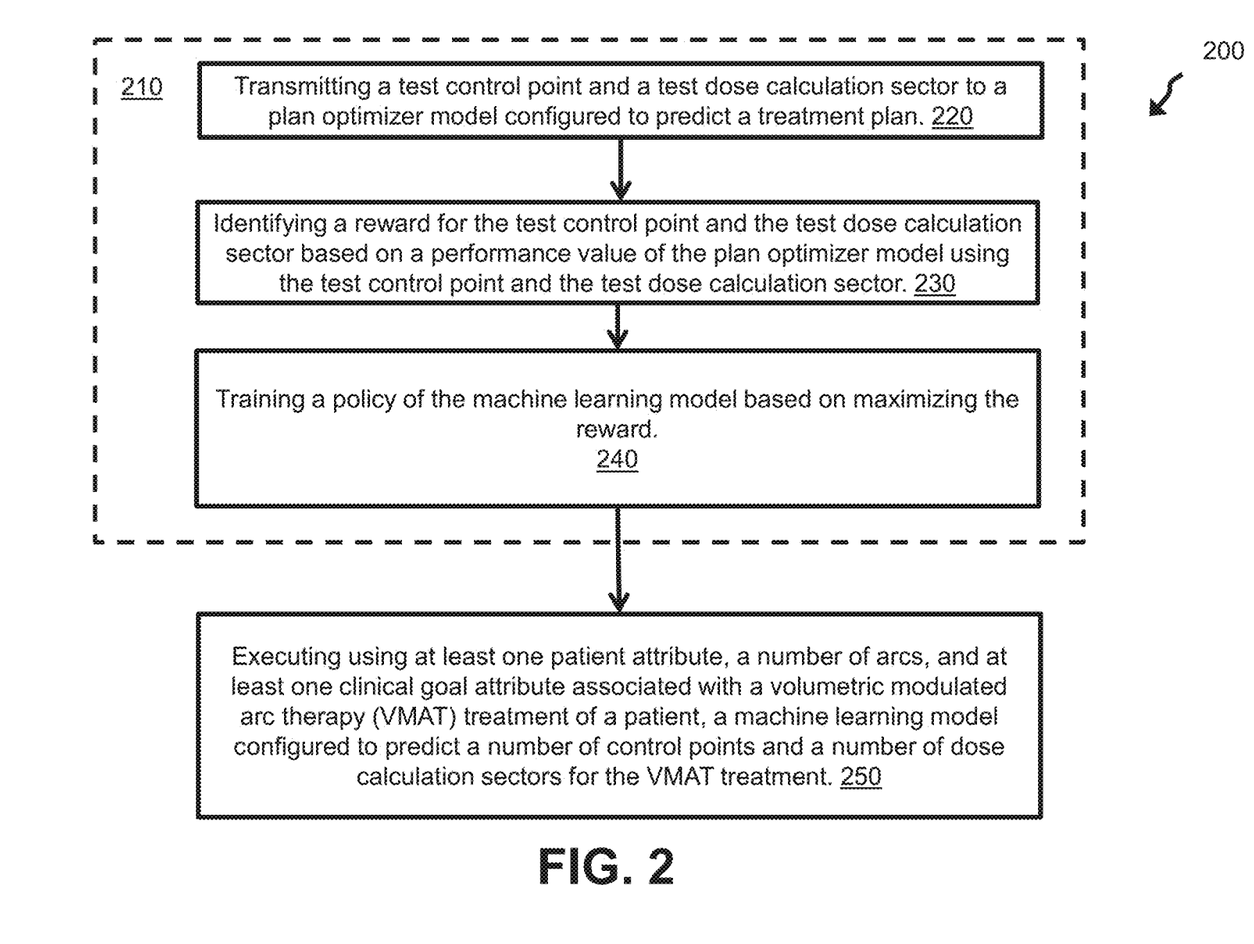
FIG. 2 illustrates a flow diagram of a process executed in an AI-enabled VMAT arc calculation system, according to an embodiment.

FIG. 2 illustrates a flow diagram of a process executed in a plan generation system, according to an embodiment. The method 200 includes steps 220-250. However, other embodiments may include additional or alternative execution steps or may omit one or more steps altogether. Before implementing/executing the AI model to predict suitable dosage sectors, the analytics server may train the AI model. The method 200 describes how an AI model may be trained (210) and then executed 250. The method 210 is described as being executed by the AI model. However, one or more steps of method 200 may also be executed by any number of computing devices operating in the distributed computing system described in FIG. 1. For instance, one or more user computing devices may locally perform part or all the steps described in FIG. 2.

The method 200 may include two phases. First the analytics server may train an AI model using a method such as a method 210 that includes steps 220-240. When the training is completed, the analytics server may then deploy the model by executing the model (step 250).

At step 220, the analytics server may transmit one or more test control points and one or more test dose calculation sectors to a plan optimizer model configured to predict a treatment plan.

The analytics server may use a reinforcement learning approach where the agent can be trained in conjunction with another model. Specifically, the agent may be trained by calculating rewards for different selected DCSs and control points where the rewards correspond to the secondary model, such as the plan optimizer model. For instance, the analytics server may first retrieve patient data and then identify rewards associated with different attributes (e.g., different DCSs and/or control points) by transmitting different iterations of values to a plan optimizer and determining how the transmitted values affect the operations of the plan optimizer and/or the overall RTTP.

The analytics server may retrieve (via a platform and/or via querying a database) patient data needed to calculate a treatment plan for the patient. Therefore, as used herein, patient data may refer to any data that is associated with the patient (e.g., the patient's physical data, diagnosis data, and any data inputted by a medical professional). In some embodiments, the analytics server may use different patient identifiers to retrieve the patient data. For instance, the analytics server may query one or more databases to identify medical data associated with the patient. The analytics server may query data associated with the patient's anatomy, such as physical data (e.g., height, weight, and/or body mass index) and/or other health-related data (e.g., blood pressure or other data relevant to receiving radiation therapy treatment). The analytics server may also retrieve data associated with current and/or previous medical treatments received by the patient (e.g., data associated with the patient's previous surgeries).

In some embodiments, the analytics server may also analyze the patient's medical data records to identify the patient attributes needed. For instance, the analytics server may query a database to identify the patient's BMI. However, because many medical records are not digitized, the analytics server may not receive the patient's BMI value using simple query techniques. As a result, the analytics server may retrieve the patient's electronic health data and may execute one or more analytical protocols (e.g., natural language processing) to identify the patient's body mass index. In another example, if the analytics server does not receive tumor data (e.g., end-points) the analytics server may execute various image recognition protocols and identify the tumor data.

The analytics server may also receive additional data from one or more medical professionals. For instance, a treating oncologist may access a platform generated/hosted by the analytics server and may add, remove, or revise data associated with a particular patient, such as patient attributes, treatment attributes, tumor attributes, the primary site of treatment, tumor stage, endpoints, whether the primary tumor has been extended, and the like. Because tumor staging and the end-level attributes are critical pieces of information that affect patient treatment, this information is typically inputted by the treating oncologist. In some embodiments, an AI model (e.g., a separate AI model that is trained to identify tumor information) may identify this information and the treating oncologist may deny, approve, or revise the predicted results. In another example, the treating oncologist may specifically indicate whether the treatment should be unilateral or bilateral.

Another example of patient data/attributes may include specific tumor locations. More specifically, this data may indicate the primary tumor location with respect to the patient's centerline. This data may be inputted by the treating oncologist or may be analyzed using various image recognition or segmentation methods executed on the patient's medical images. In some embodiments, this information can also be predicted using the AI model if it is not inputted by the treating oncologist (or otherwise received by the analytics server). Another patient attribute may indicate whether and how close the tumor is to other non-diseased organs. For instance, a tumor to be eradicated may be millimeters away from another organ. This information may change field geometry (generated by the optimizer), as other organs must be avoided.

The analytics server may deploy a plan optimizer to generate an RTTP for the patient based on the patient data. However, in order to generate the RTTP, the plan optimizer may also use CP attributes and DCSs to generate the RTTP. Therefore, in order to train the model, the analytics server and/or an agent of the AI model may first transmit a test CP attribute and/or test DCS attribute to the plan optimizer. The plan optimizer may then use the test values to generate the RTTP. The AI model may monitor the operations of the plan optimizer, such that it can gauge the test values transmitted to the plan optimizer.

In some embodiments, a single test control point and/or a single test dose calculation sector may be transmitted to the plan optimizer. Alternatively, more than a single (multiple) test control points and/or more than one test dose calculation sectors at a time. Therefore, batching test values can be done in some embodiments for more timely results.

At step 230, identifying a reward for the one or more test control points and the one or more test dose calculation sectors is identified, based on a performance value of the plan optimizer model using the one or more test control points and the one or more test dose calculation sectors. At step 240, the processor iteratively trains a policy of the artificial intelligence/machine learning model until the policy satisfies an accuracy threshold based on maximizing the reward.

As discussed herein, the training agent may use a reinforcement learning method to train itself/AI model. As used herein, the "agent" refers to the learner or the trainer (e.g., the analytics server training the AI model or the AI model itself). When training the AI model, the agent may use reinforcement learning techniques to determine when and what data points to use for training purposes. Therefore, the agent may choose between different actions and may receive a reward based on the chosen action. Using this method, the agent does not need to use a large training dataset, thereby eliminating the need to label the data.

Because the agent is using reinforcement learning methods, the agent may choose multiple actions (e.g., simultaneously) and may calculate their corresponding rewards. The agent may then calculate at least one action (or a sequence of actions) that generates the maximum reward. Through multiple iterations, the agent may learn the best actions to take.

In reinforcement learning methods described herein, the agent may interact with a possibly unknown environment (e.g., data used in conjunction with the optimizer). Therefore, the agent may implement different actions and receive corresponding rewards (e.g., the agent applies an action to the environment and receives new observations and rewards from the environment). The agent may then train itself by choosing the action(s) that provide the highest cumulative set of rewards. Throughout such a sequential decision-making process, the agent learns a policy to maximize the cumulative reward. The agent learns how to optimally decide a sequence of actions in order to get the best possible result at the end of the training process.

Throughout the training process, the agent may develop a policy (also referred to as the agent's policy). The policy is a map (expressed in various internal algorithms and mathematical formulas) from the observation space to the action space. An optimal policy guarantees receiving the most (or an optimum level of) rewards by end of the training process. Because the agent contemplates multiple variables, the policy defines how the agent must optimally decide to take an action (or a sequence of actions), such that when rewards are calculated using the multiple variables considered, the agent receives a higher (or the highest) reward. For instance, the agent may sacrifice one reward in order to gain a higher cumulative sum of rewards. Through taking actions and calculating the rewards, the agent may interact with the observation space (e.g., an unknown environment having data points that are not necessarily defined for the agent) and learns from the experience. Specifically, the agent learns (e.g., reconfigures its policy) by taking actions and analyzing the rewards received.

In an example, the agent may train itself using the action-reward system described herein. For instance, the agent receives current observation from the environment ($s_t$). The agent then executes an action ($a_t$) based on its current policy ($\pi_t$) also known as the policy or the agent's policy. Upon executing the action, the agent receives a new observation ($s_{t+1}$) and receives a reward ($r_t$). The agent then updates its policy in order to maximize the cumulative sum of future rewards. In this example, the environment follows the Markov decision process:

$$P[s_{t+1} \mid s_t] = P[s_{t+1} \mid s_1, \ldots, s_t].$$

When deciding which action yields the maximum reward, the agent may use an exploration or an exploitation methodology. The exploration method, as used herein, allows the agent to train the AI model and improve the AI model's knowledge about each data point and ability to predict accurate results. In contrast, the exploitation method chooses the greedy action (as defined below) that will obtain the greatest possible reward by exploiting the agent's current action-value estimates. Therefore, when an agent uses exploration methodology, it achieves more accurate estimates of action-values.

The analytics server may use an epsilon greedy method to train the AI model. Epsilon-greedy, as used herein, refers to an AI training method that balances exploration and exploitation. In the epsilon-greedy method, the agent may first calculate an epsilon (e) value. The e value may refer to the probability of the agent choosing to explore or exploit a data point or an action. Therefore, the E value represents a probability ratio indicating how the agent explores versus how the agent exploits. In an example, the E value may be set as 50% or 0.5. In that example, the agent explores 50% of the time and exploits 50% of the time. In contrast, an c value of 20% or 0.2 indicates that the agent explores 20% of the time and exploits 80% of the time (or vice versa, depending on how the epsilon-greedy algorithm is defined).

The analytics server may determine the e value associated with a data point. If the e value satisfies a threshold, the analytics server may generate a random, dependent result associated with the analyzed independent data point. The action taken by the analytics server in the embodiment is also referred to herein as the exploration phase.

Using the reinforcement learning methods discussed herein, the agent may train itself such that the agent can predict DCSs that yield higher rewards than other DCSs. For instance, the agent may calculate a reward for the test CP attribute and the test DCS attribute transmitted to the plan optimizer (step 220). The reward may be a quantitative assessment of the plan optimizer's performance. For instance, the reward may correspond to how fast the plan optimizer converged upon an RTTP. In another example, the reward may correspond to the quality of the RTTP. In other embodiments, the reward may correspond to any other attribute of the RTTP and/or operational parameter of the plan optimizer.

The conventional software solutions/models usually partition the arc fields into a number of equal-sized sectors according to predefined rules and thresholds that may be hard-coded into a computer model or other algorithm. For instance, a rule may indicate that there will be 16 CPs per DCS at MR level 0, 8 CPs at level 1, 4 CPs at level 2, and 2 CPs at the final MR level 3. This may be performed without considering patient-specific data or the treatment case at hand. In addition, the locations of the sectors in an arc may always remain the same; DCS subsets may then be selected at different iterations (sometimes randomly) and may be replaced with the original DCSs. Often, to ensure the reproducibility of the optimization process, the same random seeds are utilized, which results in the selection of the same set of sectors for all treatment cases. Predefined schedulers may decide (using various hardcoded algorithms that can be static) whether to proceed with the determined MR levels, e.g., based on the convergence status of the optimizer or reaching a threshold for the maximum number of iterations allowed at every MR level. While such policies may provide reasonable results for some treatment cases, they may also lead to suboptimal solutions at slow convergence rates for others.

Figure 3:
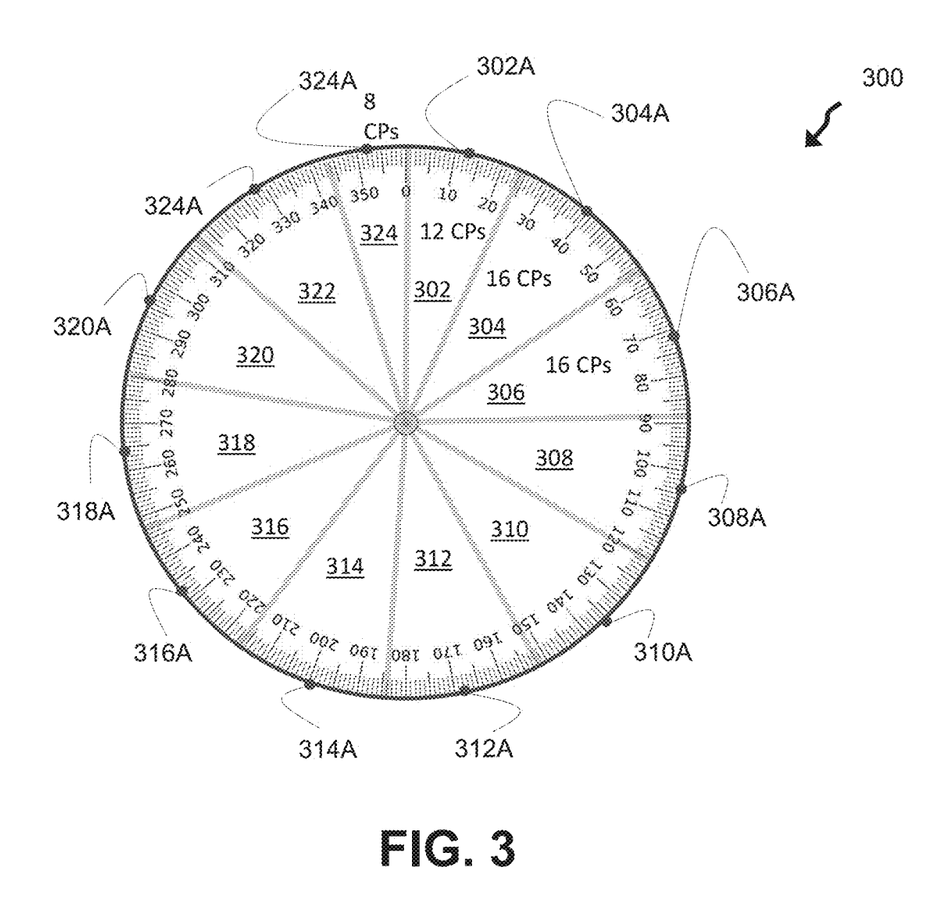
FIG. 3 illustrates different dose sectors, according to different embodiments.

FIG. 3 depicts a representation of the VMAT arc optimization. In the depicted embodiment, the arc field 300 represents 360 degrees divided into DCSs 302-324. Each arc sector may be divided into different CPs using a predetermined algorithm (e.g., designate a CP every 2 degrees). In some embodiments, the middle CP may be identified as the main CP. For instance, the processor may identify 302A-324A as the main CPs.

Figure 4:
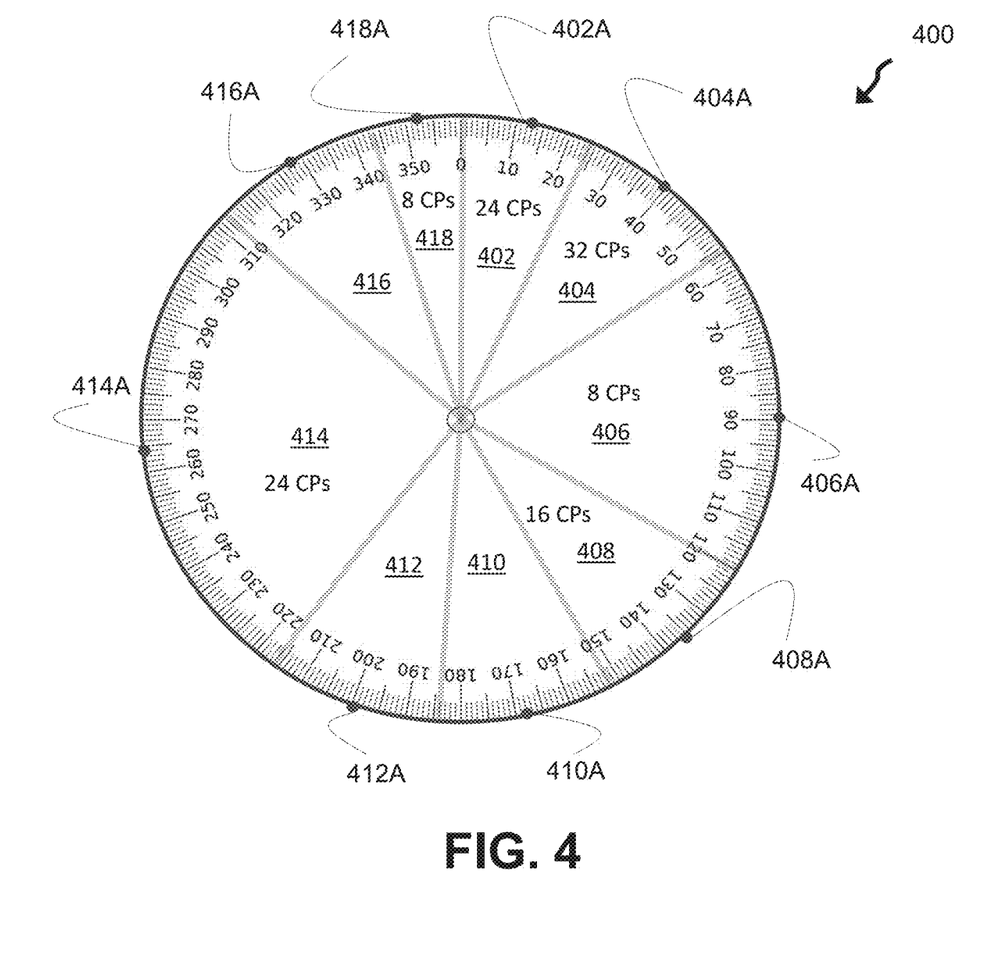
FIG. 4 illustrates different dose sectors, according to different embodiments.

FIG. 4 depicts a representation of the VMAT arc optimization using an AI model that is trained using the methods and systems discussed herein, such as the method 210. In the depicted embodiment, the arc field 400 represents 360 degrees divided into DCSs 402-418 having CPs 402A-418A. The arc field 400 may be divided using the computer models discussed herein. For instance, a computer model trained using the methods and systems discussed herein (e.g., FIGS. 1-2) can generate the boundary for the DCSs 402-418. As depicted, the DCSs are not uniformly generated. For instance, the DCS 414 has a different size than other DCSs, such as the DCS 402 or 408. This is due to the fact that the analytics server may use AI training to intelligently generate the DCSs (customized for the patient), as opposed to dividing them into equal-sized DCSs (e.g., FIG. 3).

Figure 5:
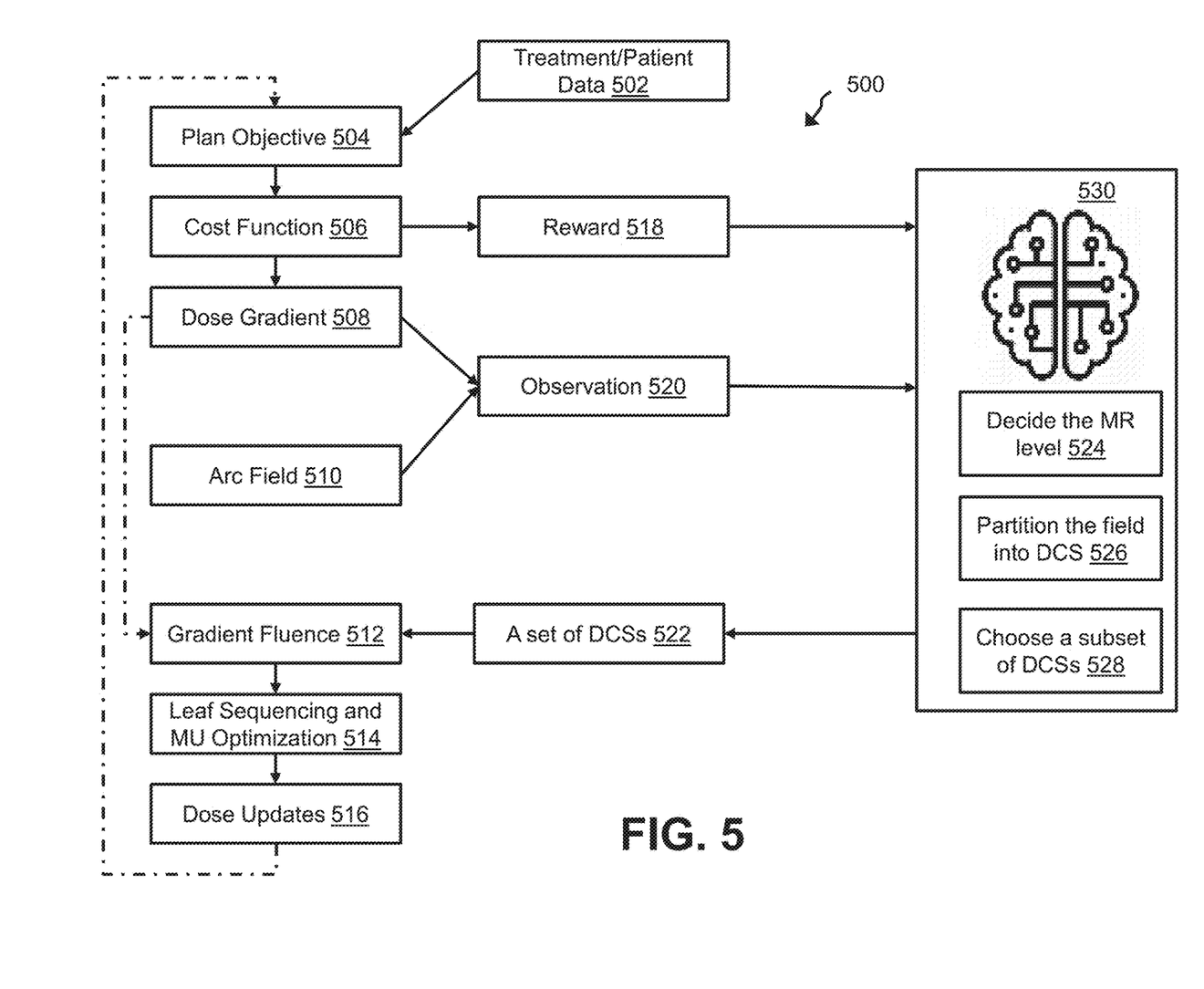
FIG. 5 illustrates different flow diagrams of different processes executed in an AI-enabled VMAT arc calculation system, according to an embodiment.

FIG. 5 depicts a representation of training the AI model discussed herein. Using the method 500, the analytics server may train an AI model (e.g., the AI model 530). When trained, the AI model 530 may decide/predict the MR level (524), intelligently partition the field into different DCSs (526), and choose a subset of DCSs (528). The method 500 may include a reinforcement learning method because this method does not require the analytics server to collect and process a training dataset. Monitoring various attributes of the radiotherapy treatment, collecting the data, processing the data, and labeling the data to train the AI model may be a time-consuming endeavor that requires high computing power.

FIG. 5 depicts how a reinforcement learning agent can be integrated into a VMAT arc optimizer to optimally and intelligently predict DCSs. During the training process, the agent may learn by trying a wide variety of sector setups for each specific treatment case in the training dataset. The agent's observation may include the arc fields (510) as well as the dose gradients (508), and calculated rewards (518) toward the plan objectives (504) and/or treatment/patient data 502 at different iterations. The agent may provide a set of non-overlapping DCS candidates (522) to be used for updating the dosage specified by a plan optimizer (516). Each sector may be specified with the starting CP number and the ending CP number within the arc. The agent may receive a reward formulated based on the reduction in the optimization cost function (506) for a set of provided DCS candidates. That is, the rewards may also be evaluated and observed (520) in light of the cost function 506 indicating how certain attributes negatively impact the patient's treatment plan (e.g., radiation interfering with OARs). As the training continues, the agent may learn an optimal policy by maximizing the cumulative sum of the rewards. Then, the agent may be tested in commissioning the sectors for cases unseen by the agent and its generalization ability may be evaluated.

With each iteration, the agent may optimize one or more parameters or attributes of the way the DCSs are predicted. As used herein, dynamic optimization parameters may refer to optimization parameters that may vary from one iteration to another. Non-limiting examples of optimization parameters may include target fluence maps (512), leaf and MU value optimization (514), dose gradients 508, number of iterations, convergence rate, and the like. At every iteration, the AI model 530 may observe a set of features extracted from the data and may provide a set of non-overlapping, optimally sized DCSs with favorable/suitable locations. In some embodiments, the AI model 530 may not necessarily maintain any set of predefined DCSs, but the non-overlapping DCSs can be of different sizes and in any location within the arc fields. This may allow for fast, comprehensive searching in the solution space of the CP parameters.

Training the AI model may also include a separate training part where the agent is observing and experimenting with a variety of possible sector setups (e.g., different permutations of DCS segmentations) and may receive a reward signal specifying how well the DCS commissioning task succeeded. Upon learning the optimal policy, the reward signal may no longer be required to execute the AI model 530. As a result, the agent can perform the task without the need for any iterative loop, which indicates that the AI model 530 is ready to be deployed.

As an example, considering different examples of RapidArc algorithms, the observation can contain target fluence maps, histories of past sectors selected, histories of how the sector leaf sequencing found improved leaf sequences, organ geometry (3D or projection images), and/or dosimetric state (e.g., how clinical goals are met). The reward used to train the agent may be a combination of the speed of convergence and quality of the solution relative to some baseline optimization results.

The AI model 530 may be trained in conjunction with the plan optimizer. Therefore, the AI model may be implemented in a manner that does not interfere with the plan optimizer's operations. How the DCSs are generated (e.g., how the entire field is segmented into different DCSs) may also affect the operation of the optimizer. For instance, the optimizer may take a different path depending on how the DCSs are (at least initially) generated and divided. Therefore, providing new data used to train the AI model during the operation of the optimizer is beneficial to training the AI model itself. Moreover, the optimizer may use an iterative process, and reinforcement learning can provide the opportunity to train the AI model as the optimizer is executing the process.

Referring back to FIG. 2, at step 250, the analytics server may execute, using at least one patient attribute, a number of arcs, and at least one clinical goal attribute associated with a VMAT treatment of a patient, an artificial intelligence model configured to predict a number of control points, and a number of dose calculation sectors for the VMAT treatment.

Using the methods and systems discussed herein, the AI model can use patient-specific data to commission/predict DCSs accordingly. Examples of patient data may include, structure volumes, dosages, plan objectives, non-target organs, dosage-related calculations (e.g., radiation dose distribution within an anatomical region of the patient), and the like. The analytics server may retrieve a patient identifier, the patient's electronic health data records, medical images (e.g., CT scans, 4D CT scans, MRIs, and X-ray images), treatment-specific data (e.g., arc information or treatment type), target organ (e.g., specification and location data to identify the tumor to be eradicated) and then transmit the data retrieved to the trained AI model.

In a non-limiting example, the analytics server may retrieve patient data and other treatment objectives (e.g., number of arcs and other clinical goals). The analytics server may then execute the trained AI model and receive a number and various attributes associated with the CPs. As used herein, attributes of the CPs may indicate how and where the CPs should be placed. For instance, an attribute may indicate a degree associated with each CP. Moreover, the trained AI model may indicate how DCSs should be segmented (e.g., start and end degrees to each DCS). The predicted data may then be displayed for a clinician. For instance, an arc field may be displayed where different CPs and DCSs are indicated, e.g., FIG. 4. Additionally or alternatively, the predicted data may be ingested by a plan optimizer, such that the plan optimizer is no longer selecting CPs and DCSs at random or using pre-determined (and often static) rules.

Figure 6:
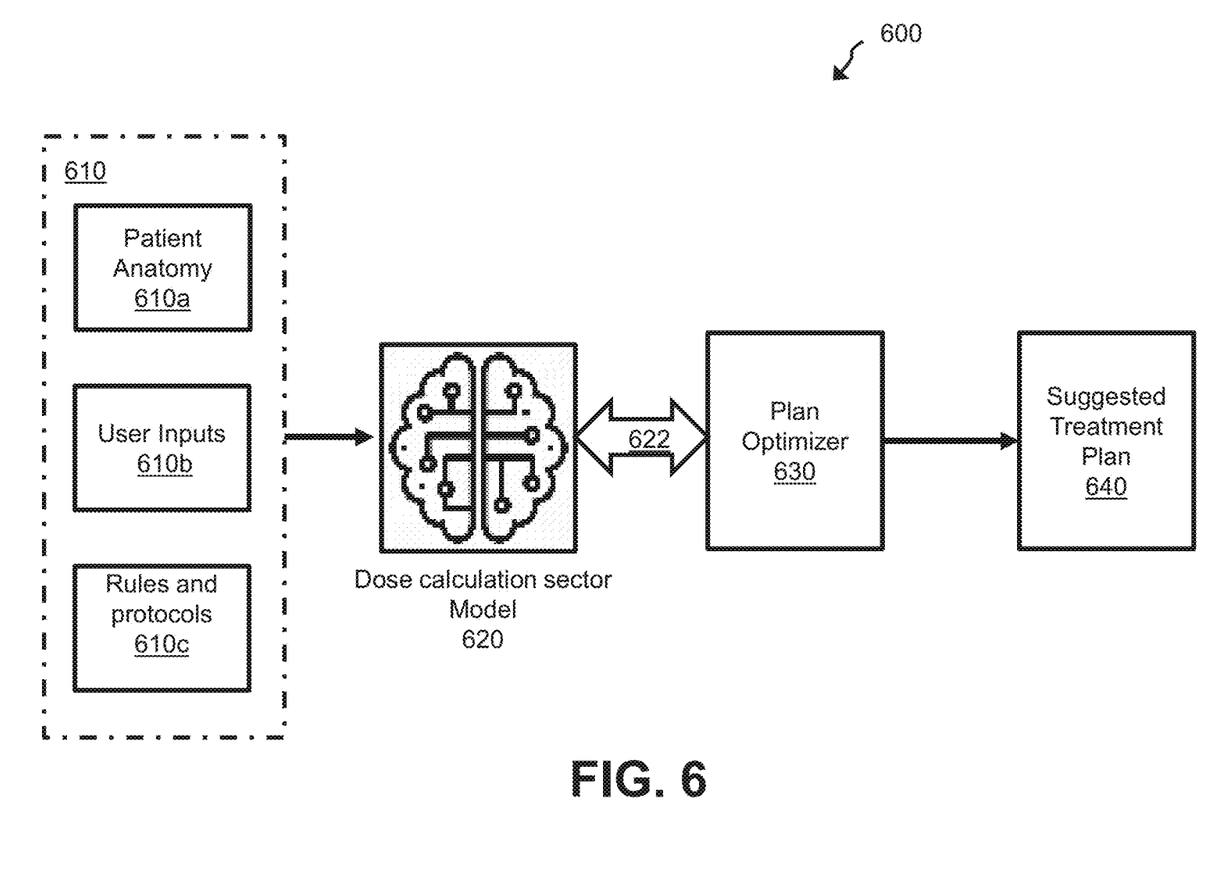
FIG. 6 illustrates different flow diagrams of different processes executed in an AI-enabled VMAT arc calculation system, according to an embodiment.

Referring now to FIG. 6, a non-limiting visual example of a workflow utilizing the methods and systems described herein is illustrated. In this non-limiting example 600, the analytics server provides dose calculation sector data to plan optimizer 630 to generate a suggested RTTP that is optimized for a patient and their treatment. The analytics server may first collect patient data 610. The patient data may include patient anatomy data 610*a* (e.g., medical images, PTVs, OARs), user inputs 610*b* (clinical objectives or rules received via a user interface from a treating oncologist, such as tumor data, PTV identification, and the like). Other non-limiting examples of clinical goals may include dosimetric goodness function, robustness metrics, biological effects of radiation, metrics of linear energy transfer, and the like. The patient data 610 may also include rules 610*c* for the patient's treatment (e.g., clinical/treatment objectives or criteria identified by the medical professionals or any other special treatments required by the medical professionals).

In some configurations, the analytics server may access a patient's internal/external file and retrieve/extract the needed patient data 610. The analytics server may then execute a dose calculation sector model 620 to identify various attributes of one or more dose calculation sectors for the patient using the patient data 610. The results generated via the dose calculation sector model 620 may be ingested by the plan optimizer 630. The plan optimizer 630 may be a treatment planning and/or monitoring software solution. The plan optimizer 630 may analyze various factors associated with the patient and the patient's treatment to generate and optimize an RTTP for the patient (e.g., field geometry, treatment modality, and radiation parameters needed to treat the patient).

One of the factors considered by the plan optimizer 630 may be the dose calculation sector attributes identified by the dose calculation sector model 620. For instance, using the dose calculation sector attributes, the plan optimizer 630 may limit its search space. As a result, the plan optimizer 630 may calculate a final beam geometry that complies with values predicted by the dose calculation sector model 620.

The plan optimizer 630 may iteratively revise the patient's RTTP wherein the plan optimizer 630 iteratively revises different attributes of the RTTP (e.g., field geometry). In some configurations, the plan optimizer 630 may transmit new treatment plan data back to the dose calculation sector model 620, whereby the dose calculation sector model 620 can recalculate/re-predict data based on the revised treatment data generated by the plan optimizer (iteration 622). The plan optimizer 630 and the dose calculation sector model 620 may repeat the iteration 622 until the patient's RTTP is optimized.

When the plan optimizer 630 completes the patient's RTTP, the plan optimizer 630 may transmit the suggested treatment plan 640 to one or more electronic devices where a user (e.g., clinician) can review the suggested plan. For instance, the suggested treatment plan 640 (or any attributes predicted by the dose calculation sector model 620) may be displayed on a computer of a clinic where a radiation therapy technician or a treating oncologist can review the data.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:
executing, by a processor, using at least one patient attribute, a number of arcs, and at least one clinical goal attribute associated with a volumetric modulated arc therapy (VMAT) treatment of a patient, an artificial intelligence model configured to predict a number of control points and a number of dose calculation sectors for the VMAT treatment, the artificial intelligence model having been iteratively trained using a reinforcement learning method, where with each iteration, the artificial intelligence model:
transmits one or more test control points and one or more test dose calculation sectors to a plan optimizer model configured to predict a treatment plan; and
identifies a reward for the one or more test control points and the one or more test dose calculation sectors based on a performance value of the plan optimizer model using the one or more test control points and the one or more test dose calculation sectors,
wherein the processor iteratively trains a policy of the artificial intelligence model based on maximizing the reward.

2. The method of claim 1, further comprising:
transmitting, by the processor, the number of control points and the number of dose calculation sectors for the VMAT treatment to the plan optimizer model.

3. The method of claim 1, wherein the reward is based on whether the plan optimizer model converges upon a predicted treatment plan.

4. The method of claim 1, wherein the reward is based on an execution time of the plan optimizer model.

5. The method of claim 1, wherein the artificial intelligence model is configured to predict a degree associated with at least one control point.

6. The method of claim 1, further comprising:
displaying, by the processor, a visual representation of at least one dose calculation sector.

7. The method of claim 1, further comprising:
displaying, by the processor, a visual representation of at least one control point.

8. A system comprising:
a server in communication with an artificial intelligence model, where the server is configured to:
execute using at least one patient attribute, a number of arcs, and at least one clinical goal attribute associated with a volumetric modulated arc therapy (VMAT) treatment of a patient, the artificial intelligence model configured to predict a number of control points and a number of dose calculation sectors for the VMAT treatment, the artificial intelligence model having been iteratively trained using a reinforcement learning method, where with each iteration, the artificial intelligence model:
transmits one or more test control points and one or more test dose calculation sectors to a plan optimizer model configured to predict a treatment plan; and
identifies a reward for the one or more test control points and the test one or more dose calculation sectors based on a performance value of the plan optimizer model using the one or more test control point and the one or more test dose calculation sectors,
wherein the processor iteratively trains a policy of the artificial intelligence model based on maximizing the reward.

9. The system of claim 8, wherein the server is further configured to:
transmit the number of control points and the number of dose calculation sectors for the VMAT treatment to the plan optimizer model.

10. The system of claim 8, wherein the reward is based on whether the plan optimizer model converges upon a predicted treatment plan.

11. The system of claim 8, wherein the reward is based on an execution time of the plan optimizer model.

12. The system of claim 8, wherein the artificial intelligence model is configured to predict a degree associated with at least one control point.

13. The system of claim 8, wherein the server is further configured to:
display a visual representation of at least one dose calculation sector.

14. The system of claim 8, wherein the server is further configured to:
display a visual representation of at least one control point.

15. A system comprising:
one or more processors; and
a non-transitory memory configured to store computer code instructions, the computer code instructions when executed cause the one or more processors to:
execute using at least one patient attribute, a number of arcs, and at least one clinical goal attribute associated with a volumetric modulated arc therapy (VMAT) treatment of a patient, an artificial intelligence model configured to predict a number of control points and a number of dose calculation sectors for the VMAT treatment, the artificial intelligence model having been iteratively trained using a reinforcement learning method, where with each iteration, the artificial intelligence model:
transmits one or more test control points and one or more test dose calculation sectors to a plan optimizer model configured to predict a treatment plan; and
identifies a reward for the one or more test control points and the one or more test dose calculation sectors based on a performance value of the plan optimizer model using the one or more test control points and the one or more test dose calculation sectors,
wherein the processor iteratively trains a policy of the artificial intelligence model based on maximizing the reward.

16. The system of claim 15, wherein the computer code instructions further cause the one or more processors to:
transmit the number of control points and the number of dose calculation sectors for the VMAT treatment to the plan optimizer model.

17. The system of claim 15, wherein the reward is based on whether the plan optimizer model converges upon a predicted treatment plan.

18. The system of claim 15, wherein the reward is based on an execution time of the plan optimizer model.

19. The system of claim 15, wherein the artificial intelligence model is configured to predict a degree associated with at least one control point.

20. The system of claim 15, wherein the computer code instructions further cause the one or more processors to:
display a visual representation of at least one dose calculation sector.

* * * * *